(12) United States Patent
Nakatani et al.

(10) Patent No.: US 9,057,105 B2
(45) Date of Patent: Jun. 16, 2015

(54) METHOD FOR DETECTING SINGLE NUCLEOTIDE POLYMORPHISM IN NUCLEIC ACID

(71) Applicants: FURUKAWA ELECTRIC ADVANCED ENGINEERING CO., LTD., Ichihara-shi, Chiba (JP); OSAKA UNIVERSITY, Suita-shi, Osaka (JP)

(72) Inventors: Kazuhiko Nakatani, Suita (JP); Fumie Takei, Suita (JP); Chikara Dohno, Suita (JP); Xi Chen, Suita (JP)

(73) Assignees: FURUKAWA ELECTRIC ADVANCED ENGINEERING CO., LTD., Ichihara-Shi (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/352,208

(22) PCT Filed: Mar. 8, 2013

(86) PCT No.: PCT/JP2013/056423
§ 371 (c)(1),
(2) Date: Apr. 16, 2014

(87) PCT Pub. No.: WO2013/133402
PCT Pub. Date: Sep. 12, 2013

(65) Prior Publication Data
US 2014/0255938 A1    Sep. 11, 2014

(30) Foreign Application Priority Data

Mar. 8, 2012 (JP) .................................. 2012-051551

(51) Int. Cl.
*C12Q 1/68* (2006.01)
*C07H 21/00* (2006.01)
(Continued)

(52) U.S. Cl.
CPC ................ *C12Q 1/6883* (2013.01); *C12Q 1/68* (2013.01); *G01N 33/53* (2013.01); *G01N 33/542* (2013.01)

(58) Field of Classification Search
CPC ...... C12Q 1/68; C12Q 1/6816; C12Q 1/6827; C12Q 1/6844; C12Q 1/6853; C12Q 1/686; C07H 21/00; C07H 21/02; C07H 21/04
USPC ................ 435/6.1, 91.2; 536/22.1, 23.1, 24.3
See application file for complete search history.

(56) References Cited

U.S. PATENT DOCUMENTS

| | | | |
|---|---|---|---|
| 5,866,336 A * | 2/1999 | Nazarenko et al. | 435/6.12 |
| 2003/0148301 A1 | 8/2003 | Aono et al. | |
| 2010/0015618 A1 * | 1/2010 | Nakatani et al. | 435/6 |

FOREIGN PATENT DOCUMENTS

| | | |
|---|---|---|
| JP | 2004-236655 A | 8/2004 |
| WO | WO 01/42498 A1 | 6/2001 |
| WO | WO 2006/082685 A1 | 8/2006 |

OTHER PUBLICATIONS

Kobori et al., The SPR Sensor Detecting Cytosine-Cytosine Mismatches. JACS 126 :557 (2004).*

(Continued)

*Primary Examiner* — Ethan C Whisenant
(74) *Attorney, Agent, or Firm* — Birch, Stewart, Kolasch & Birch, LLP

(57) ABSTRACT

A method for detecting a single nucleotide polymorphism in nucleic acids, characterized in that the method includes mixing (A) a nucleic acid probe comprising a nucleotide sequence complementarily hybridizable to an evaluation subject nucleic acid/an antisense strand thereof containing at least one single nucleotide polymorphism, and tagged with a nucleotide sequence of a hairpin structure having a bulge at a 5'-terminal thereof, wherein a guanine residue is introduced at an adjoining position of the bulge, and wherein a naphthyridine derivative compound is immobilized to the bulge; and (B) the evaluation subject nucleic acids; and detecting a signal ascribed to the naphthyridine derivative compound when the above nucleic acid probe and the above evaluation subject nucleic acids are hybridized, thereby evaluating the above single nucleotide polymorphism.

7 Claims, 5 Drawing Sheets

(51) Int. Cl.
*C07H 21/02* (2006.01)
*C07H 21/04* (2006.01)
*G01N 33/53* (2006.01)
*G01N 33/542* (2006.01)

(56) References Cited

OTHER PUBLICATIONS

Nazarenko et al. A closed tube format for amplification and detection of DNA based on energy transfer. Nucleic Acids Research 25 (12) ::2516 (1997).*

Sobrino SNPs in forensic genetics: a review on SNP typing methodologies. Forensic Science Intl. 154 : 181 (2005).*

Suda et al. N,N'-Bis(3-aminopropyI)-2,7-diamino-1,8-naphthyridine stabilized a single pyrimidine bulge in duplex DNA. Bioorganic & Medicinal Chemistry 13 :4507 (2005).*

Takei et al., Allele Specific C-Bulge Probeswith One Unique Fluorescent Molecule Discriminate the Single Nucleotide Polymorphism in DNA. Chemistry A European Journal 13 : 4452(2007).*

Fumie Takei et al.; "Hairpin Tag o Motsu Primer o Tsukatta Ichi Enki Takei no Keiko Kenshutsu" The 90th Annual Meeting of the Chemical Society of Japan in Spring (2010) Koen Yokoshu III, Mar. 12, 2010, p. 758.

International Search Report issued in PCT/JP2013/056423, mailed May 28, 2013.

* cited by examiner

SEQUENCE LISTING

```
<160> NUMBER OF SEQ ID NOS: 8

<210> SEQ ID NO 1
```

-continued

```
<211> LENGTH: 19
<212> TYPE: DNA
<213> ORGANISM: Artificial
<220> FEATURE:
<223> OTHER INFORMATION: a sequence of synthetic DNA (tag sequence)

<400> SEQUENCE: 1
atcatgcttt tgccatgat                                                  19

<210> SEQ ID NO 2
<211> LENGTH: 10
<212> TYPE: DNA
<213> ORGANISM: Artificial
<220> FEATURE:
<223> OTHER INFORMATION: a sequence of synthetic DNA (template)

<400> SEQUENCE: 2
tccatgcaac                                                            10

<210> SEQ ID NO 3
<211> LENGTH: 11
<212> TYPE: DNA
<213> ORGANISM: Artificial
<220> FEATURE:
<223> OTHER INFORMATION: a sequence of synthetic DNA (C bulge)

<400> SEQUENCE: 3
gttgccatgg a                                                          11

<210> SEQ ID NO 4
<211> LENGTH: 11
<212> TYPE: DNA
<213> ORGANISM: Artificial
<220> FEATURE:
<223> OTHER INFORMATION: a sequence of synthetic DNA (A bulge)

<400> SEQUENCE: 4
gttgacatgg a                                                          11

<210> SEQ ID NO 5
<211> LENGTH: 11
<212> TYPE: DNA
<213> ORGANISM: Artificial
<220> FEATURE:
<223> OTHER INFORMATION: a sequence of synthetic DNA (G bulge)

<400> SEQUENCE: 5
gttggcatgg a                                                          11

<210> SEQ ID NO 6
<211> LENGTH: 11
<212> TYPE: DNA
<213> ORGANISM: Artificial
<220> FEATURE:
<223> OTHER INFORMATION: a sequence of synthetic DNA (T bulge)

<400> SEQUENCE: 6
gttgtcatgg a                                                          11

<210> SEQ ID NO 7
<211> LENGTH: 36
<212> TYPE: DNA
<213> ORGANISM: Artificial
<220> FEATURE:
<223> OTHER INFORMATION: a sequence of synthetic DNA (primer 1)

<400> SEQUENCE: 7
```

```
atcatgcttt tgccatgatc aggaaacagc tatgac                              36
```

<210> SEQ ID NO 8
<211> LENGTH: 20
<212> TYPE: DNA
<213> ORGANISM: Artificial
<220> FEATURE:
<223> OTHER INFORMATION: a sequence of synthetic DNA (M13M3)

<400> SEQUENCE: 8

```
gttgtaaaac gacggccagt                                                20
```

METHOD FOR DETECTING SINGLE NUCLEOTIDE POLYMORPHISM IN NUCLEIC ACID

TECHNICAL FIELD

The present invention relates to a method for detecting a single nucleotide polymorphism in nucleic acids to be a target, and a kit therefor. More particularly, the present invention relates to a method for conveniently and highly sensitively detecting a single nucleotide polymorphism in nucleic acids to be a target and a kit therefor.

BACKGROUND ART

A single nucleotide polymorphism is a difference among the individuals existing on a genomic DNA, which may cause differences in various diseases and various phenotypes in human and the like. Therefore, the SNP is utilized in analysis of genetic diseases, discriminations between the individuals, and the like.

At present, real-time PCR method used in the detection of a single nucleotide polymorphism (SNP) include, for example, Taq Man (Registered Trademark) method and SYBR (Registered Trademark) Green method. The Taq Man (Registered Trademark) method is a highly sensitive method: however, the design and synthesis of Taq Man (Registered Trademark) probe used in the detection are complicated, thereby making the detection cost high. In addition, the SYBR (Registered Trademark) Green method is a convenient method utilizing that fluorescent intensity increases by the binding of a double-stranded DNA; however, formation of double strands by nonspecific amplification would also be detected as being "positive," the detection error is large, so that there is a problem of optimizing the primers used for increases allelic specificity. As the primers in these methods, fairly correct primers to some degree are designed using designing software, and thereafter the primer sequences and conditions for PCR are optimized so that the allelic specificity would be the highest. However, optimization on individual genomes would be necessitated, so much works are needed to find optimal conditions.

By contrast, the present inventors have reported a hairpin primer PCR (HP-PCR) method utilizing the fluorescent properties that compounds containing a naphthyridine ring specifically bind to bulge structures, thereby shifting from a wavelength of maximum absorbance before binding, and that the fluorescent intensity fluctuates depending upon the kinds of nucleotide residues pairing with nucleotides adjoining the bulge nucleotide (see Patent Publication 1). Concretely, first, primers having a hairpin structure in which a bulge region to which the compounds containing a naphthyridine ring specifically bind is introduced at a 5'-terminal are prepared, and next, the subject nucleic acids are hybridized by PCR to form a duplex containing a bulge structure. The naphthyridine ring-containing compounds are added thereto and bound to the bulge structure, thereby shifting the wavelength of maximum absorbance, which is observed as fluctuations of fluorescent intensities.

PRIOR ART REFERENCES

Patent Publications

Patent Publication 1: WO 2006/082685

SUMMARY OF THE INVENTION

Problems to be Solved by the Invention

In the method of Patent Publication 1, primers having a hairpin structure are inexpensive and readily available, and the method can be carried out according to simple procedures of simply mixing the primers, samples, and the naphthyridine ring-containing compounds. However, in the binding of the naphthyridine ring-containing compounds and the bulge structure, there exists an equilibrium:

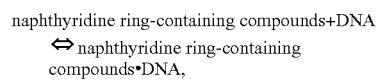

so that excess naphthyridine ring-containing compounds would be required during PCR. Therefore, the fluorescence of the naphthyridine ring-containing compounds non-binding to the bulge structure is detected as a background, so that there is a disadvantage in lowering the detection sensitivity.

An object of the present invention is to provide a method for conveniently and highly sensitively detecting a single nucleotide polymorphism and genes in the nucleic acids to be a target.

Means to Solve the Problems

As a result of studies, the present inventors have found that a naphthyridine ring-containing compound is previously bound to a particular position of the primer having a hairpin structure used in PCR, whereby the hairpin structure opens by the progress of PCR and a bulge structure disappears, thereby resulting in freeing the naphthyridine ring-containing compound to recover fluorescence, making it possible to perform monitoring on changes in fluorescent intensities of only the fluorescent-labeled primers, so that the detection errors can be markedly reduced. The present invention has been perfected thereby.

Concretely the present invention relates to the following [1] to [2]:

[1] a method for detecting a single nucleotide polymorphism in nucleic acids, characterized in that the method includes:

mixing (A):

i) a nucleic acid probe containing a nucleotide sequence complementarily hybridizable to an evaluation subject nucleic acid containing at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; or ii) a nucleic acid probe containing a nucleotide sequence complementarily hybridizable to an antisense strand of an evaluation subject nucleic acid containing at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and (B) the above evaluation subject nucleic acids; and detecting a signal ascribed to the 2,7-diaminonaphthyridine derivative compound due to the disappearance of the above cytosine bulge or thymine bulge when the above nucleic acid probe and the evaluation subject nucleic acids are hybridized, thereby evaluating the above single nucleotide polymorphism.

[2] a kit for use in a method for detecting a single nucleotide polymorphism in nucleic acids of the above [1], containing:

i') a nucleic acid probe containing a nucleotide sequence complementarily hybridizable to an evaluation subject nucleic acid containing at least one single nucleotide polymorphism, and containing a wild-type nucleotide at a single nucleotide polymorphism-existing position, and tagged with a nucleotide sequence of a hairpin structure having a cytosine bulge or thymine bulge at a 5'-terminal thereof,
wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and ii') a nucleic acid probe containing a nucleotide sequence complementarily hybridizable to an antisense strand of an evaluation subject nucleic acid containing at least one single nucleotide polymorphism, and containing a wild-type nucleotide at a single nucleotide polymorphism-existing position, and tagged with a nucleotide sequence of a hairpin structure having a cytosine bulge or thymine bulge at a 5'-terminal thereof,
wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge;
and i") a nucleic acid probe containing a nucleotide sequence complementarily hybridizable to an evaluation subject nucleic acid containing at least one single nucleotide polymorphism, and containing a mutant nucleotide at a single nucleotide polymorphism-existing position, and tagged with a nucleotide sequence of a hairpin structure having a cytosine bulge or thymine bulge at a 5'-terminal thereof,
wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and ii") a nucleic acid probe containing a nucleotide sequence complementarily hybridizable to an antisense strand of an evaluation subject nucleic acid containing at least one single nucleotide polymorphism, and containing a mutant nucleotide at a single nucleotide polymorphism-existing position, and tagged with a nucleotide sequence of a hairpin structure having a cytosine bulge or thymine bulge at a 5'-terminal thereof,
wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge.

Effects of the Invention

According to the method for detection of the present invention, some excellent effects that a single nucleotide polymorphism in nucleic acids can be detected at low costs, conveniently and highly sensitively. In addition, the method for detecting a single nucleotide polymorphism of the present invention is a florescence-increasing type PCR detection method, in which the design of the primers is simple and competitive primers are present within the PCR tube, whereby allelic specificity can be greatly improved, thereby making it possible to solve conventional problems such as monitoring amplification of other genes, needing to study the conditions in order to increase allelic specificity, and further having difficulty in designing of the primers.

MODES FOR CARRYING OUT THE INVENTION

Figure 1:
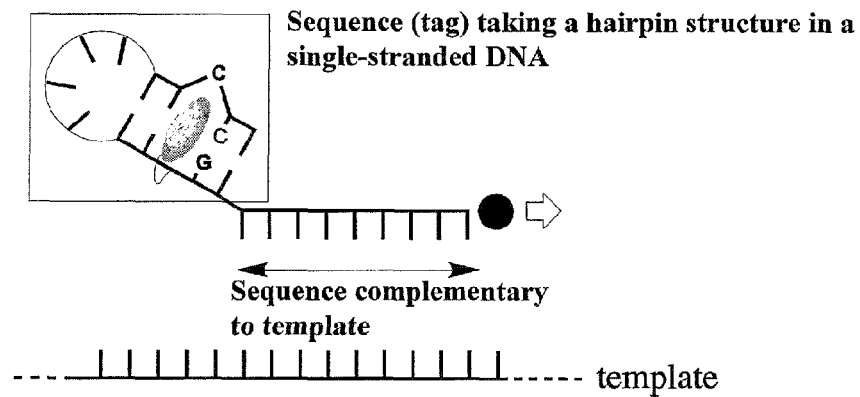
FIG. 1 is a diagram showing a schematic view of a nucleic acid probe in the present invention.

The method for detecting a single nucleotide polymorphism of the present invention is PCR method using allele-specific primers having a hairpin structure at a 5'-terminal, which has a feature in that the primers are probes in which a naphthyridine ring-containing compound is previously bound at a particular position of the hairpin structure.

If a naphthyridine ring-containing compound is chemically immobilized near the bulge, the absolute amount of the naphthyridine ring-containing compound is equivalent to the amount of the primers, so that there would be no problem such as an increase in background level by fluorescent intensity of the naphthyridine ring-containing compound existing in excess in the solution, as compared to a case of free form.

Also, in the present invention, a phenomenon in which fluorescence is quenched when the naphthyridine ring-containing compound binds to the bulge, in a case where the base pairs before and after bulge are particular base pairs, is utilized. In other words, positions before and after bulge are particular base pairs, thereby fluorescent intensity by the naphthyridine ring-containing compound is kept small before performing PCR. Next, the reaction for PCR progresses and a hairpin structure is opened by a polymerase, a naphthyridine ring-containing compound previously bound to the bulge is migrated to external of a DNA double strand, so that inherently owned fluorescence would be observed.

The method for detecting a single nucleotide polymorphism of the present invention includes mixing (A) a particular nucleic acid probe and (B) an evaluation subject nucleic acid, and detecting a signal caused when the nucleic acid probe and the evaluation subject nucleic acid are hybridized.

The nucleic acid probe usable in the present invention includes the following embodiments.

i) a nucleic acid probe containing a nucleotide sequence complementarily hybridizable to an evaluation subject nucleic acid containing at least one single nucleotide polymorphism, and tagged with a nucleotide sequence of a hairpin structure having a cytosine bulge or thymine bulge at a 5'-terminal thereof,
wherein a guanine residue is introduced at a position adjoining 5' or 3'-terminal side of the cytosine bulge or thymine bulge, and wherein a 2,7-diaminonaphthyridine derivative compound is introduced to the cytosine bulge or thymine bulge; and ii) a nucleic acid probe containing a nucleotide sequence complementarily hybridizable to an antisense strand of an evaluation subject nucleic acid containing at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3% terminal side of the cytosine bulge or thymine bulge, and wherein a 2,7-diaminonaphthyridine derivative compound is immobilized to the cytosine bulge or thymine bulge.

Here, the term "nucleotide" as used herein refers to deoxyribonucleotide, unless specified otherwise. Therefore, the terms "cytosine" (C), "thymine" (T), "adenine" (A), and "guanine" (G) as used herein respectively mean each of the deoxyribonucleotides, namely "2'-deoxycytidine," 2'-deoxythymidine," "2'-deoxyadenosine" and "2'-deoxyguanosine," respectively, unless specified otherwise.

In addition, the phrase "evaluation subject nucleic acid containing at least one single nucleotide polymorphism" as used herein refers to a nucleic acid in which the presence of at least one, preferably one to five single nucleotide polymorphisms, is confirmed, and the nucleotide existing at a position of a single nucleotide polymorphism, unless specified otherwise, includes both wild-type nucleotides and mutant nucleotides. Further, the phrase "wild-type nucleotide at a single nucleotide polymorphism-existing position" as used herein refers to a nucleotide at a site where a single nucleotide polymorphism is confirmed, which is a nucleotide at the site in a so-called normal type nucleotide sequence, and the phrase "mutant nucleotide at a single nucleotide polymorphism-existing position" refers to a nucleotide at the site where a single nucleotide polymorphism is confirmed, which is a nucleotide at the site in a so-called mutant nucleotide sequence.

Furthermore, the phrase "cytosine bulge or thymine bulge" as used herein refers to a region that does not form a base pair in a DNA forming a double strand in which the other strand is in excess of cytosine or thymine as compared to one strand. Accordingly, the nucleotide sequence of the hairpin structure (also referred to as hairpin sequence) having the cytosine bulge or thymine bulge may be those having sequences in which a double strand is formed by hybridization in an autologous sequence in the order of terminal nucleotides themselves of 5'-terminal or 3'-terminal of the hairpin sequence, thereby forming the hairpin structure, and being capable of forming double strand (duplex) having a cytosine bulge or thymine bulge in the course of the double strand. Concretely, included are, for example, both terminals of a single-stranded DNA themselves being hybridized to form a double strand having a cytosine bulge or thymine bulge, DNA located more centrally than the region of the cytosine bulge or thymine bulge existing in the form of single strand.

The nucleic acid probe usable in the present invention contains a part having a nucleotide sequence complementarily hybridizable to the evaluation subject nucleic acid itself or an antisense strand thereof in the backbone thereof. More particularly, the nucleic acid probe includes, depending upon the kinds of the evaluation subject nucleic acid, those containing a part having a nucleotide sequence complementarily hybridizable to a wild-type (normal) evaluation subject nucleic acid and an antisense strand thereof, and a part having a nucleotide sequence complementarily hybridizable to a mutant evaluation subject nucleic acid and an antisense strand thereof. Further, depending upon the kinds of the single nucleotide polymorphism of the evaluation subject nucleic acid, the nucleic acid probe includes those containing a wild-type nucleotide at a single nucleotide polymorphism-existing position and those containing a mutant nucleotide at a single nucleotide polymorphism-existing position. Here, the term "antisense strand" refers to a nucleotide having a nucleotide sequence complementary to a particular nucleotide sequence (hereinafter referred to as sense sequence), and being capable of hybridizing to the sense strand.

Next, in the nucleic acid probe in the present invention, a nucleotide sequence of a hairpin structure having a cytosine bulge or thymine bulge at a 5'-terminal thereof is further tagged with a nucleotide sequence complementarily hybridizable to the evaluation subject nucleic acid or an antisense strand thereof (see FIG. 1). In the present specification, the tagged sequence is also written as "tag structure." Here, the nucleotide sequence of the nucleic acid probe is not particularly limited, and one having desired sequences can be prepared according to a known method such as a thiophosphite method or a phosphoamidite method. For example, the nucleotide sequence can be prepared by designing a nucleotide sequence obtained by tagging a nucleotide sequence of a tag structure which can form a double strand by hybridization in the order from 5'-terminal and 3'-terminal nucleotides themselves in an autologous sequence, thereby forming a hairpin structure, and can form a double strand (duplex) having a cytosine bulge or thymine bulge in the course of the double strand, to a nucleotide sequence complementarily hybridizable to an evaluation subject thereof or an antisense strand thereof. The nucleotide sequence of tag structure is not particularly limited, so long as the nucleotide sequences forms the above hairpin structure, including, for example, a sequence as shown in:

```
5'- ATCATGCTTTTGCCATGAT- 3'    (SEQ ID NO: 1)
```

In the above sequence, for example, a 2,7-aminonaphthyridine derivative compound mentioned later is immobilized to the sequence at a position of fifth T from the 5'-terminal to allow sixth C from the 3'-terminal to form a bulge structure.

The tag structure in the present invention shows a hairpin structure containing a cytosine bulge or thymine bulge, and a 2,7-diaminonaphthyridine derivative compound is immobilized to the cytosine bulge or thymine bulge. Here, the immobilization of the compound to the cytosine bulge or thymine bulge as used herein includes an embodiment of binding the compound to cytosine or thymine that does not form a base pair in the bulge to be immobilized, an embodiment of binding the compound to a nucleotide adjoining the bulge to be immobilized to a bulge region, and an embodiment of binding the compound to both the nucleotides to be immobilized.

The 2,7-diaminonaphthyridine derivative compound in the present invention includes compounds represented by the formula (I):

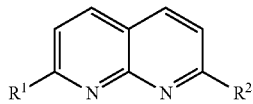

wherein each of $R^1$ and $R^2$ is independently a primary amine residue, a secondary amine residue, or a tertiary amine residue.

The above primary amine residue includes an —$NH_2$ group. In addition, the above secondary amine residue includes, for example, an $NH(CH_2)_3NH_2$ group, an —$NH(CH_2)_4NH_2$ group, an —$NH(CH_2)_2NH_2$ group, an —$NH(CH_2)_2NH(CH_3)$ group, and the like. Further, the above tertiary amine residue includes, for example, an —$N(CH_3)(CH_2)_2NH_2$ group, and the like. In the present invention, the secondary amine residue is preferred, and both $R^1$ and $R^2$ are more preferably secondary amine residues, from the viewpoint of formation of hydrogen bonding with a cytosine bulge or thymine bulge.

The above 2,7-diaminonaphthyridine derivative compound concretely includes N,N'-bis-3-aminopropyl-2,7-diamino-1,8-naphthyridine represented by the following formula (II):

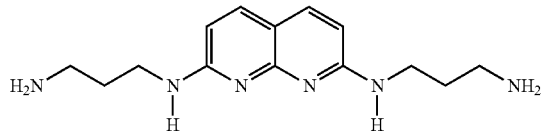

(hereinafter also referred to as DANP).

The N,N'-bis-3-aminopropyl-2,7-diamino-1,8-naphthyridine (DANP) has a hydrogen bond on the nitrogen side at N1-position or N8-position of the naphthyridine ring in the order of donor, acceptor, acceptor, and donor, so that a double-stranded DNA, preferably a stable complex having a stoichiometric ratio of 1:1 with a cytosine bulge or thymine bulge is formed.

Figure 2:
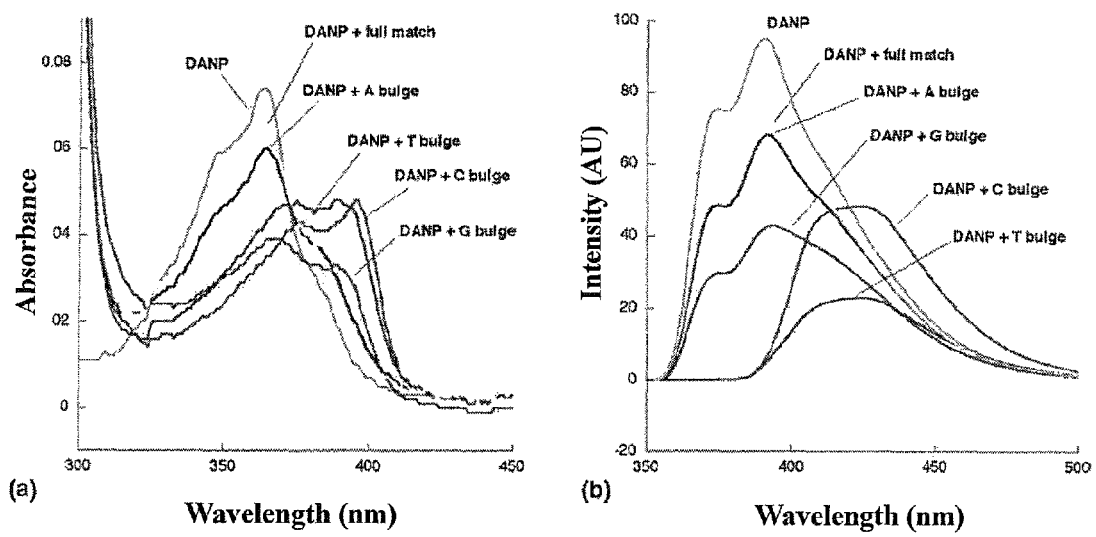
FIG. 2 is graphs showing optical properties of N,N'-bis-3-aminopropyl-2,7-diamino-1,8-naphthyridine (DANP).

In addition, for example, in the measurements of a ultraviolet-visible light absorption spectrum in a 10 mM sodium phosphate buffer (pH 7.0) [see FIG. 2(a)], DANP has properties that shows an absorption maximum at 364 nm when used alone, but has a reduced absorbance and shifts an absorption maximum on a long-wavelength side of that alone by 30 nm to 394 nm when, for example, binding to a cytosine bulge DNA, and also shifts an absorption maximum to 390 nm in the same manner as binding to a thymine bulge DNA. Furthermore, in the measurements of the fluorescence spectrum excited at a wavelength 364 nm corresponding to the absorption maximum of DANP alone [see FIG. 2(b)], a maximum luminescence is shown at 394 nm when used alone, but a wide luminescence is observed at around 424 nm when, for example, binding to a cytosine bulge DNA, and a wide luminescence is observed upon binding to a thymine bulge DNA at a wavelength nearly the same as a cytosine bulge DNA binding, albeit weakly. Thus, according to the characteristic luminescence shown by DANP-cytosine bulge binding and DANP-thymine bulge binding, each of DANP alone, DANP-cytosine bulge binding, and DANP-thymine bulge binding can be discriminated. Here, the optical properties upon cytosine bulge or thymine bulge binding are not limited by the kinds of the nucleotides adjoining the cytosine bulge DNA or thymine bulge DNA, and the wavelength of the absorption maximum may fluctuate for about 2 to about 3 nm.

As DANP, one synthesized by the method described in Japanese Patent Laid-Open No. 2004-262827 may be used.

Here, in the present invention, a derivative compound of the above DANP can be used, so long as the derivative compound has properties equivalent to those of the above DANP, in other words, the properties such as, for example, fluorescence is generated, binding capacity to a bulge is possessed, and the absorption maximum wavelength shifts by binding to a bulge, and at the same time the fluorescent intensity changes depending upon allele. Examples of such a derivative compound include a compound represented by the following formula (III):

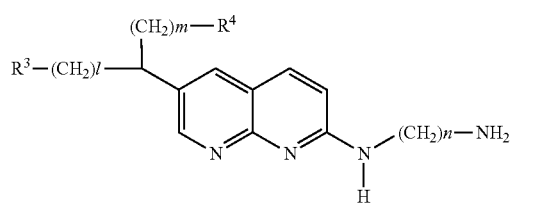

wherein each of $R^3$ and $R^4$ is independently a hydrogen atom or an amino group, and each of l, m and n is independently a natural number of from 1 to 6;

a compound represented by the following formula (IV):

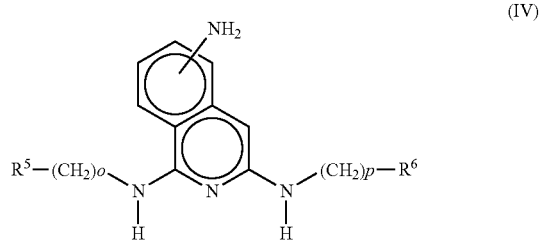

wherein each of $R^5$ and $R^6$ is independently a hydrogen atom or an amino group, and each of o and p is independently a natural number of from 1 to 6;
and the like.

In the compound represented by the formula (III), each of the above $R^3$ and $R^4$ is independently a hydrogen atom or an amino group, and it is desirable that one of them is preferably an amino group, from the viewpoint of fully exhibiting the properties such as fluorescence is generated, binding capacity to a bulge is possessed, and the absorption maximum wavelength shifts by binding to a bulge, and at the same time the fluorescent intensity changes depending upon alleles. In addition, each of the above l, m and n is independently a natural number of from 1 to 6. The above l is preferably 2 or more, more preferably 3 or more, and preferably 6 or less, and more preferably 5 or less, and even more preferably 4 or less, and concretely, preferably from 2 to 6, more preferably from 3 to 5, and even more preferably from 3 to 4, from the viewpoint of fully exhibiting the properties such as fluorescence is generated, binding capacity to a bulge is possessed, and the absorption maximum wavelength shifts by binding to a bulge, and at the same time the fluorescent intensity changes depending upon alleles. In addition, the above m is preferably 2 or more, and more preferably 3 or more, and preferably 6 or less, more preferably 5 or less, and even more preferably 4 or less, and concretely, preferably from 2 to 6, more preferably from 3 to 5, and even more preferably from 3 to 4, from the viewpoint same as the above. Furthermore, the above n is preferably 2 or more, and more preferably 3 or more, and preferably 6 or less, more preferably 5 or less, and even more preferably 4 or less, and concretely, preferably from 2 to 6, more preferably from 3 to 5, and even more preferably from 3 to 4, from the same viewpoint as the above.

In the compound represented by the formula (IV), each of the above $R^5$ and $R^6$ is independently a hydrogen atom or an amino group, and it is desirable that at least one of them is preferably an amino group, from the viewpoint of fully exhibiting the properties such as fluorescence is generated, binding capacity to a bulge is possessed, and the absorption maximum wavelength shifts by binding to a bulge, and at the same time the fluorescent intensity changes depending upon alleles. In addition, each of the above o and p is independently a natural number of from 1 to 6. The above o is preferably 2 or more, and more preferably 3 or more, and preferably 6 or less, more preferably 5 or less, and even more preferably 4 or less, and concretely, preferably from 2 to 6, more preferably from 3 to 5, and even more preferably from 3 to 4, from the viewpoint of fully exhibiting the properties such as fluorescence is generated, binding capacity to a bulge is possessed, and the absorption maximum wavelength shifts by binding to a bulge, and at the same time the fluorescent intensity changes depending upon alleles. In addition, the above p is preferably 2 or more, and more preferably 3 or more, and preferably 6 or less, more preferably 5 or less, and even more preferably 4 or less, and concretely, preferably from 2 to 6, more preferably from 3 to 5, and even more preferably from 3 to 4, from the same viewpoint as the above.

In addition, in the present invention, as the above 2,7-diaminonaphthyridine derivative compound, N,N'-bis-3-aminobutyl-2,7-diamino-1,8-naphthyridine represented by the following formula (V):

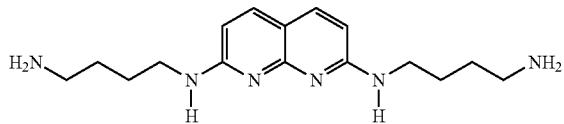

(V)

is also preferably used.

A compound represented by formula (V) also forms a stable complex having a stoichiometric ratio of 1:1 with a double-stranded DNA, preferably a cytosine bulge or thymine bulge, as in the same manner with DANP.

The ultraviolet-visible light absorption spectrum of the compound represented by formula (V) is nearly the same as that of DANP, and fluctuations of the absorption maximum wavelength by binding to a bulge is also about the same level as that of DANP.

Here, the compound represented by the formula (V) can be synthesized according to a known method.

Figure 3:
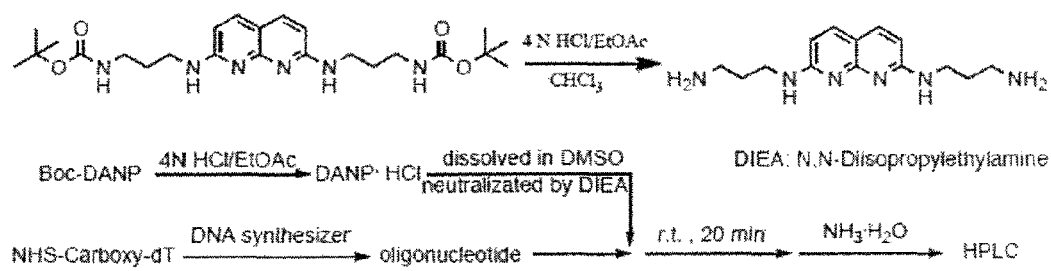
FIG. 3 is schematic view of immobilizing a 2,7-diaminonaphthyridine derivative compound to DNA.

The method for immobilizing the above 2,7-diaminonaphthyridine derivative compound to a cytosine bulge or thymine bulge is not limited specifically, but includes a known method for modifying a compound on a DNA, for example, a post-modification method using reaction of an active carboxylic acid and amine. Concretely, for example, as shown in FIG. 3, after each of a target DNA and a 2,7-diaminonaphthyridine derivative compound is synthesized, the DNA is immersed in a solution of the 2,7-diaminonaphthyridine derivative compound (for example, an acetonitrile solution) at room temperature, preferably at from 15° to 30° C., for from 10 to 20 minutes, and purified as needed, whereby the 2,7-diaminonaphthyridine derivative compound can be immobilized to a cytosine bulge or thymine bulge by a hydrogen bond.

In addition, in the above tag structure, a guanine residue is introduced at a position adjoining 5' or 3'-terminal side of the cytosine bulge or thymine bulge. In other words, a guanine-cytosine (G-C) base pair is formed at a position adjoining 5' or 3'-terminal side of the cytosine bulge or thymine bulge to which the 2,7-diaminonaphthyridine derivative compound is immobilized. In general, it is known that, when an aromatic molecule is inserted between a double-stranded DNA, electronic state of the molecule is affected by stacking interaction of the nucleotides adjoining the inserted position. Accordingly, it is made possible to quench fluorescence generated when the above 2,7-diaminonaphthyridine derivative compound binds to a cytosine bulge or thymine bulge. In the present invention, it is preferred that the 2,7-diaminonaphthyridine derivative compound is immobilized by an adjoining nucleotide on the opposite side to the side on which a guanine-cytosine (G-C) base pair is formed, and cytosine or thymine of the bulge, from the viewpoint of ensuring the quenching effect by the guanine residue.

Figure 4:
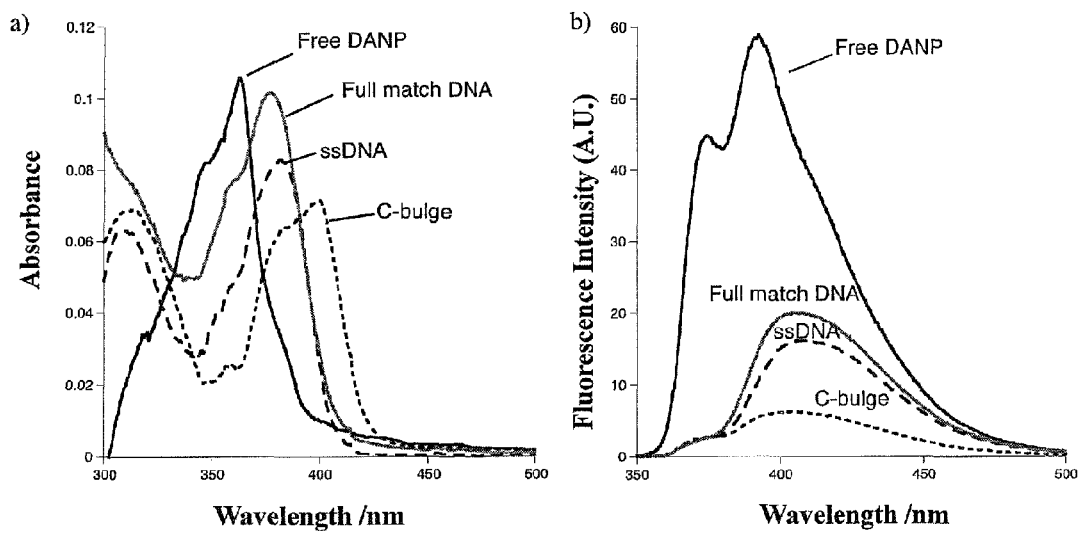
FIG. 4 is graphs showing optical properties during bulge DNA binding where an adjoining position of N,N'-bis-3-aminopropyl-2,7-diamino-1,8-naphthyridine is a guanine residue.

For example, in the measurements of the ultraviolet-visible light absorption spectrum in a 10 mM sodium phosphate buffer (pH 7.0) [see FIG. 4 (a)], for a case of a single-stranded DNA (ssDNA) wherein DANP is bound to a cytosine bulge DNA, a case of a duplex by a nucleotide sequence wherein the region other than the nucleotide sequence having the above cytosine bulge DNA-DANP and the bulge region is complementary and wherein a guanine residue is introduced at the position adjoining the bulge (C-bulge), and a case of a duplex by a nucleotide sequence completely complementary to a nucleotide sequence having the above cytosine bulge DNA-DANP (full-match), it can be seen that each absorption maximum is as follows: DANP alone is 364 nm, and both of ssDNA and full-match are 380 nm, whereas C-bulge is 400 nm. In addition, in the measurements of the fluorescence spectrum excited at a wavelength 364 nm corresponding to the absorption maximum of DANP alone [see FIG. 4 (b)], DANP alone shows the maximum luminescence at 393 nm and the intensity of 58. On the other hand, it can be seen that all the maximum luminescence of ssDNA, full-match and C-bulge are 410 nm, while the intensity is 16, 20 and 6, respectively, the intensity of C-bulge being the weakest and about one-tenth that of DANP alone. Thus, when the 2,7-diaminonaphthyridine derivative compound is immobilized to a cytosine bulge or thymine bulge, luminescence of the 2,7-diaminonaphthyridine derivative compound is quenched by introducing a guanine residue at an adjoining position.

The length of the above nucleic acid probe is preferably 15 nucleotide residues or more, more preferably 20 nucleotide residues or more, and preferably 45 nucleotide residues or less, more preferably 40 nucleotide residues or less, from the viewpoint of fully exhibiting sufficient stability and high sequence specificity to a bulge DNA.

Figure 5:
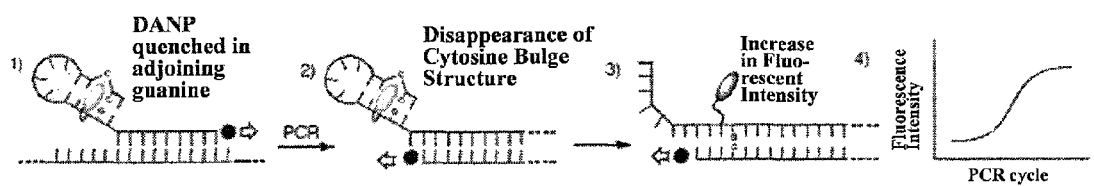
FIG. 5 is diagrams showing the summary of the method for detecting a single nucleotide polymorphism of the present invention according to the present invention.

In the method for detecting a single nucleotide polymorphism of the present invention, (A) a nucleic acid probe having the optical properties described above and (B) evaluation subject nucleic acids are mixed and hybridized, and a signal ascribed to the 2,7-diaminonaphthyridine derivative compound due to the disappearance of a cytosine bulge or thymine bulge is detected accompanying the progress of PCR. In other words, in the detection method of the present invention, as shown in FIG. 5, a prepared (A) nucleic acid probe and (B) evaluation subject nucleic acids are mixed and hybridization progresses [see FIG. 5(1)], and a hairpin structure of the (A) nucleic acid probe is opened and the bulge structure of the cytosine bulge or thymine bulge is disappeared [see FIG. 5 (2)], whereby the 2,7-diaminonaphthyridine derivative compound previously bound to the bulge structure is migrated to external of a double strand [see FIG. 5 (3)], so that the fluorescent intensity of the 2,7-diaminonaphthyridine derivative compound is measured [see FIG. 5 (4)].

It is preferable that the mixing of the (A) nucleic acid probe and the (B) evaluation subject nucleic acids is carried out in a manner that a molar ratio thereof, i.e. (A)/(B), is about 1/1, in order to sufficiently carry out the formation of a double strand and sufficiently obtain a fluorescent intensity, and the mixing is not unconditionally determined depending upon the kinds or amount of the evaluation subject nucleic acids.

The pH conditions upon mixing is preferably 5 or more, more preferably 6 or more, and even more preferably 6.5 or more, from the viewpoint of efficiently carrying out detection of the signal of the 2,7-diaminonaphthyridine derivative compound, shift of the absorption maximum wavelength ascribed to binding of the compound to a bulge, fluorescent intensity and the like, and from the viewpoint of stability of nucleic acids, and preferably 9 or less, more preferably 8 or less, and even more preferably 7.5 or less, from the viewpoint of sufficiently releasing the 2,7-diaminonaphthyridine derivative compound from the bulge structure, and from the viewpoint of exhibiting sufficient fluorescent intensity.

Upon the above mixing, for example, a phosphate buffer, Tris-HCl buffer or the like can be used.

In the present specification, hybridization means that one nucleic acid molecule having a certain sequence and another nucleic acid molecule complementary to at least a portion of the above nucleic acid molecule are associated via a hydrogen bond on the basis of nucleotide sequences complementary to each other. It is desirable that hybridization in the present invention is carried out in a buffer having a pH of from 5 to 8, and preferably a pH of from 6 to 7, containing from 1 mM to 1 M, and preferably from 10 to 100 mM sodium chloride, and the buffer is preferably phosphate buffer. Here, the hybridizable conditions can be appropriately optimized according to a known technique.

As a signal ascribed to the 2,7-diaminonaphthyridine derivative compound by disappearance of a cytosine bulge or thymine bulge, a fluorescent signal is preferred. The fluorescent signal has a fluorescent intensity at preferably from 400 to 480 nm, more preferably at around 450 nm, in both cases of a cytosine bulge and a thymine bulge, from the viewpoint of sufficiently increasing difference in the fluorescent intensity derived from a free 2,7-diaminonaphthyridine derivative compound and a 2,7-diaminonaphthyridine derivative compound bound to a cytosine bulge or thymine bulge and moreover quenched by guanine of an adjoining nucleotide. Here, the excitation wavelength can be appropriately adjusted on the basis of the kind of the 2,7-diaminonaphthyridine derivative compound.

Thus, according to the present invention, an excellent effect that a single nucleotide polymorphism can be detected without separately adding a labeling substance such as a fluorescent substance is exhibited, by using a 2,7-diaminonaphthyridine derivative compound. Therefore, in the detection method of the present invention, a single nucleotide polymorphism can be conveniently detected without carrying out a complicated step such as studies on conditions for elongation reaction, amplification reaction, and enzyme reaction (for example, the above elongation reaction, amplification reaction, degradation reaction of mismatched nucleic acids and the like), studies on electrophoresis conditions, and labeling with a labeling substance. Furthermore, since the above 2,7-diaminonaphthyridine derivative compound binds to a cytosine bulge or thymine bulge having a guanine residue at the adjoining position and is quenched before PCR reaction, background signal level is lowered, thereby enabling highly sensitive detection of a single nucleotide polymorphism.

In another embodiment of the detection method of the present invention, the method includes identifying a single nucleotide polymorphism in an evaluation subject nucleic acid on the basis of a signal ascribed to the 2,7-diaminonaphthyridine derivative compound when hybridizing each of 1) a wild-type evaluation subject nucleic acid containing a wild-type nucleotide in a single nucleotide polymorphism-existing position, and a nucleic acid probe complementarily hybridizable to the wild-type evaluation subject nucleic acid;
2) a mutant evaluation subject nucleic acid containing a mutant nucleotide in a single nucleotide polymorphism-existing position, and a nucleic acid probe complementarily hybridizable to the mutant evaluation subject nucleic acid;
3) the wild-type evaluation subject nucleic acid and a nucleic acid probe complementarily hybridizable to the mutant evaluation subject nucleic acid; and
4) the mutant evaluation subject nucleic acid and a nucleic acid probe complementarily hybridizable to the wild-type evaluation subject nucleic acid.

Concretely, for example, fluorescence with high intensity ascribed to the 2,7-diaminonaphthyridine derivative compound is emitted, only in the case where hybridization is carried out to the nucleic acid probe in the present invention in a single nucleotide polymorphism-existing position of the evaluation subject nucleic acid. In other cases, the 2,7-diaminonaphthyridine derivative compound binds to a cytosine bulge or thymine bulge within the probe, and the fluorescence is quenched. Therefore, evaluation of a single nucleotide polymorphism can be highly sensitively carried out, depending upon the kind of the base pair at the single nucleotide polymorphism-existing position in the probe.

In addition, in the present invention, a kit for use in the method for detecting a single nucleotide polymorphism in the nucleic acids of the present invention is provided. The kit of the present invention is characterized in that the kit contains the above nucleic acid probe, and exhibits excellent effects that the detection method of the present invention can be efficiently and conveniently carried out at low cost, and that a single nucleotide polymorphism in nucleic acids can be efficiently and highly sensitively detected at low cost according to simple procedures.

Concretely, included are:
i') a nucleic acid probe containing a nucleotide sequence complementarily hybridizable to an evaluation subject nucleic acid containing at least one single nucleotide polymorphism, and containing a wild-type nucleotide at a single nucleotide polymorphism-existing position, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and ii') a nucleic acid probe containing a nucleotide sequence complementarily hybridizable to an antisense strand of an evaluation subject nucleic acid containing at least one single nucleotide polymorphism, and containing a wild-type nucleotide at a single nucleotide polymorphism-existing position, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and i") a nucleic acid probe containing a nucleotide sequence complementarily hybridizable to an evaluation subject nucleic acid containing at least one single nucleotide polymorphism, and containing a mutant nucleotide at a single nucleotide polymorphism-existing position, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and ii") a nucleic acid probe containing a nucleotide sequence complementarily hybridizable to an antisense strand of an evaluation subject nucleic acid containing at least one single nucleotide polymorphism, and containing a mutant nucleotide at a single nucleotide polymorphism-existing position, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge.

The kit of the present invention may appropriately contain a reagent for stably retaining the above nucleic acid probe, for example, a buffer or the like.

In addition, the form for providing the kit may be a form provided as one container including all of the reagents appropriate for carrying out the detection method of the present invention such as an appropriate nucleic acid probe and a necessary reagent in a volume and/or form appropriate for carrying out the detection method of the present invention, or may be a form provided by containers, each of which independently contains a nucleic acid probe, a reagent or the like. In addition, such a kit may include instructions in which the procedures and the like for carrying out the detection method of the present invention using the components contained in the kit are described.

EXAMPLES

The present invention will be explained hereinafter on the basis of Example, without intending to limit the scope of the present invention to these Examples or the like.

Test Example 1

The fluorescent intensity of a nucleotide sequence wherein DANP is bound to a nucleotide sequence having a cytosine bulge, thymine bulge, guanine bulge or adenine bulge was measured.

As for synthesis of a 10 mer template nucleic acid (xcD1) as shown in SEQ ID NO: 2, those having a desired sequence were synthesized with a DNA synthesizer (manufactured by Applied Biocyctems Inc.), using NHS-Carboxy-dT amidite (manufactured by Glen Research Corporation). Here, since deprotection of adenine amidite and guanine amidite is easy, a product which was pac-protected was used. Processing and deprotection were not carried out on the DNA synthesizer, and a column containing CPG beads was removed at a stage where a DNA was bound to CPG resin. A syringe was connected one each to both ends of this column, and 1 mL of the above DANP solution was repeatedly moved in the two syringes, and allowed to react in that state for 20 minutes. Thereafter, the reaction mixture was dried with a vacuum pump, and the beads were transferred to an Eppendorf (Registered Trademark) tube and treated with 1 mL of a 28% aqueous ammonia. The mixture was allowed to stand at room temperature for 3 hours, whereby processing and deprotection were carried out. Thereafter, the CPG beads were removed by filtration, the mixture was concentrated with SpeedVac and subjected to HPLC purification, to prepare a probe xcD1 (SEQ ID NO: 2), in which DANP was bound to position 5 of T located at a fifth base from the 5'-terminal. Here, confirmation of the resulting probe was carried out using MALDI TOF/MS. Next, a nucleotide sequence capable of forming a cytosine bulge, thymine bulge, guanine bulge or adenine bulge as shown in SEQ ID NOs: 3 to 6 was synthesized in the same manner.

(template) xcD1: 5'-TCCATGCAAC-3' (SEQ ID NO: 2)

(C bulge) cD1-1: 5'-GTTGCCATGGA-3' (SEQ ID NO: 3)

(A bulge) cD1-3: 5'-GTTGACATGGA-3' (SEQ ID NO: 4)

(G bulge) cD1-4: 5'-GTTGGCATGGA-3' (SEQ ID NO: 5)

(T bulge) cD1-5: 5'-GTTGTCATGGA-3' (SEQ ID NO: 6)

The resulting nucleic acid capable of forming a bulge (SEQ ID NOs: 3 to 6) and a template nucleic acid (SEQ ID NO: 2) were hybridized in an Eppendorf tube. Thereafter a solution of the hybridized product was prepared to have 4.5 µM in a 10 mM sodium phosphate buffer (pH 7.0), and the fluorescence spectrum excited at a wavelength 380 nm was measured. The results are shown in FIG. 6.

Figure 6:
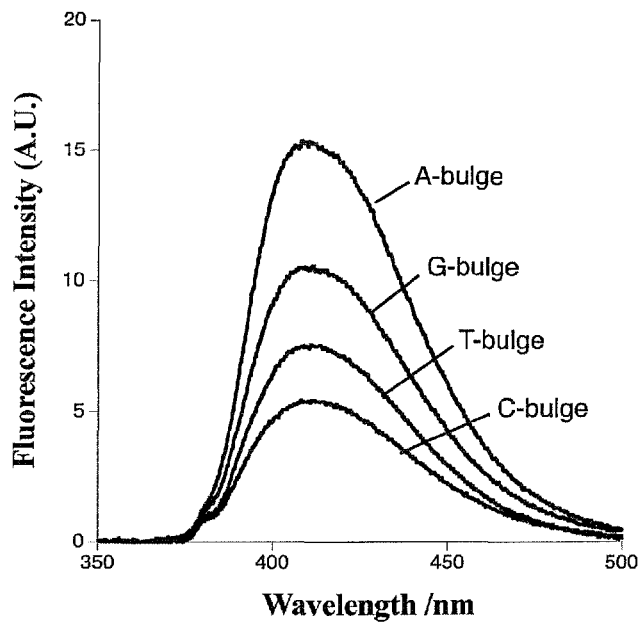
FIG. 6 is a graph showing quenching of fluorescence depending upon the kinds of bulge DNA.

According to FIG. 6, it can be seen that the fluorescent intensity is the weakest in a cytosine bulge, next are in a thymine bulge and a guanine bulge, and the strongest in an adenine bulge.

Preparation Example 1 of Nucleic Acid Probe

In accordance with the method described in Japanese Patent Laid-Open No. 2004-262827, N,N'-bis-3-aminopropyl-2,7-diamino-1,8-naphthyridine of which amino group was Boc-protected was synthesized, and thereafter deprotected with a 4 N HCl solution, to give DANP hydrochloride. The resulting DANP hydrochloride was dissolved in dimethyl sulfoxide, and the solution was then neutralized with N,N-diisopropylethylamine, to prepare a solution of DANP (concentration: 0.1 M).

Next, in order to carry out PCR with pUC18 (having SNP of guanine at position 464) as a template, a probe capable of forming a cytosine bulge structure in which DANP was bound to position 5 of T located at a fifth base from the 5'-terminal [primer 1 (SEQ ID NO: 7)] was prepared using the DNA synthesizer in the same manner as Test Example 1. Here, confirmation of the concentration of the probe was carried out using enzymatic degradation.

```
(primer 1):
                                            (SEQ ID NO: 7)
5'- ATCATGCTTTTGCCATGATCAGGAAACAGCTATGAC- 3'
```

Test Example 1 of PCR

Figure 7:
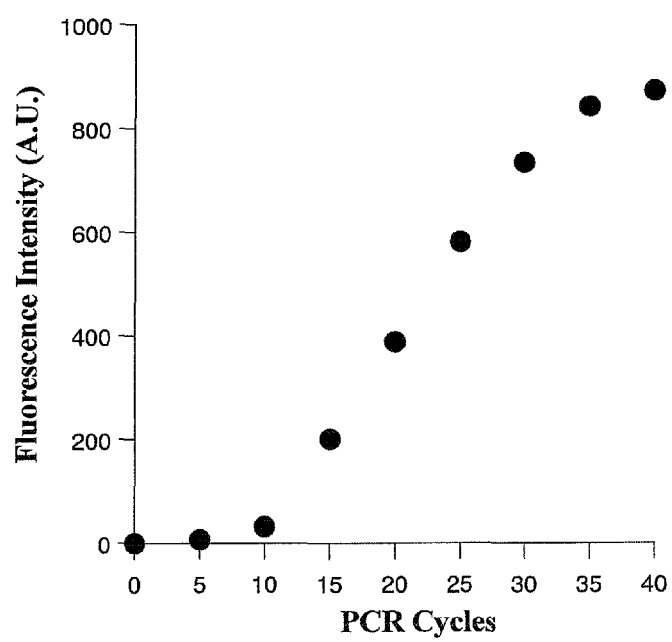
FIG. 7 is a graph showing changes in fluorescent intensities accompanying progress of PCR using the method for detection of the present invention.

PCR was carried out using the resulting nucleic acid probe (a primer having a hairpin tag containing a cytosine bulge structure at the 5'-terminal) (primer 1). Concretely, using pUC18 as a template, each of Taq PCR Master Mix from QIAGEN, a sense primer having a hairpin tag (primer 1) and an antisense primer having no hairpin tag [M13M3 (SEQ ID NO: 8)] at final concentrations of 0.5 µM, and pUC18 were added, to prepare a PCR solution. The PCR solution was heated at 95° C. for 1 minute, and thereafter 40 cycles of reaction, wherein one cycle comprises 95° C. for 10 seconds, 55° C. for 30 seconds, and 72° C. for 30 seconds, were carried out. A sample was collected every 5 cycles, and a fluorescent intensity (excitation wavelength: 355 nm, emission wavelength: 450 nm) was measured. As a result, an increase in the fluorescent intensity was observed with the progress of PCR (FIG. 7).

```
(primer 1):
                                            (SEQ ID NO: 7)
5'- ATCATGCTTTTGCCATGATCAGGAAACAGCTATGAC- 3'

(M13M3):
                                            (SEQ ID NO: 8)
5'- GTTGTAAAACGACGGCCAGT- 3'
```

Test Example 2 of PCR

Figure 8:
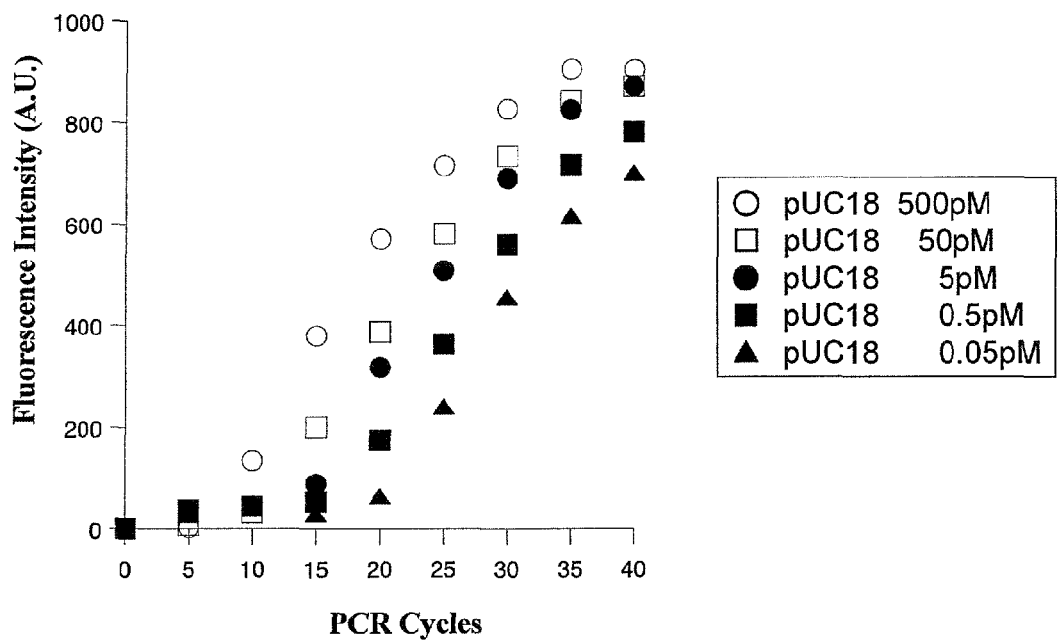
FIG. 8 is a graph showing changes in fluorescent intensities accompanying progress of PCR when the amount of the evaluation subject nucleic acid is varied.
Figure 9:
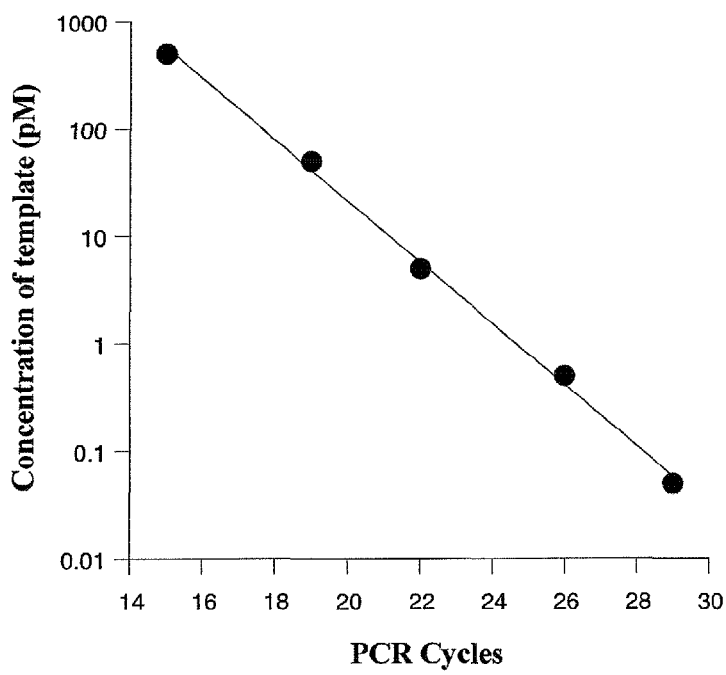
FIG. 9 is a graph showing the number of PCR performed until a given fluorescent intensity is reached.

PCR was carried out in the same manner as in Test Example 1 of PCR, except that only the amount of the template was changed. A graph obtained by plotting fluorescent intensity of every fifth cycle (excitation wavelength: 355 nm, emission wavelength: 450 nm) against the number of PCR cycles is shown in FIG. 8. FIG. 9 is a graph obtained by plotting the amount of the template at a point where the fluorescent intensity was 380 on the axis of ordinates against PCR cycles on the axis of abscissas.

According to FIG. 8, it can be seen that a profile of change in the fluorescent intensity reflecting the concentration of the template was observed when solutions only differing in template concentrations were prepared and PCR was carried out. In addition, according to FIG. 9, as a result of plotting the amount of the template at a point where the fluorescent intensity of FIG. 8 was 380 against PCR cycles, nearly a linear graph was obtained, suggesting that the fluorescent intensity could be quantified at least within the range of the concentration of the used template.

Test Example 3 of PCR

Figure 10:
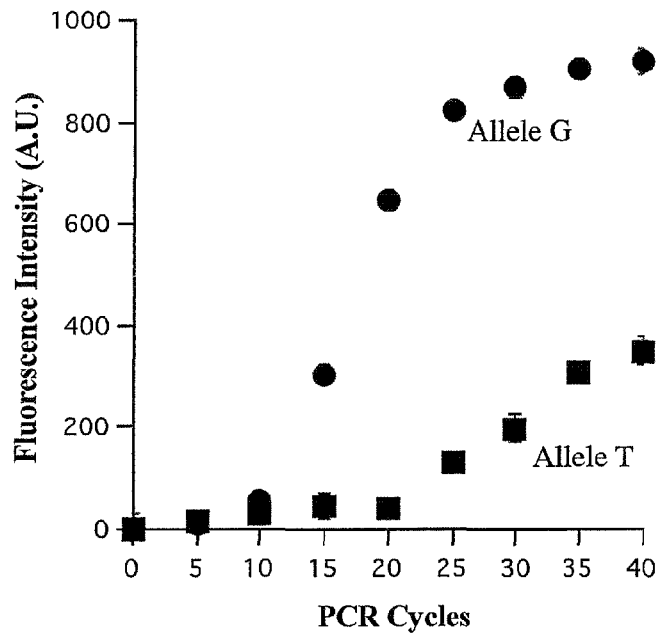
FIG. 10 is a graph showing changes in fluorescent intensities accompanying progress of PCR when SNPs of the evaluation subject nucleic acid are different.

PCR was carried out in the same manner as Test Example 1 of PCR, using a template of which SNP site was mutated from guanine to thymine in Test Example 1. A graph obtained by plotting fluorescent intensity of every fifth cycle (excitation wavelength: 355 nm, emission wavelength: 450 nm) against the number of PCR cycles is shown in FIG. 10. According to FIG. 10, it is suggested that increase in the fluorescent intensity is clearly small as compared with the case where the template is matched with the 3'-terminal of the primer, and that SNP detection is made possible with this primer.

Test Example 4 of PCR

Using N,N-bis-3-aminobutyl-2,7-diamino-1,8-naphthyridine (a compound represented by the formula (V)) synthesized referring to the synthesis method of DANP, a nucleic acid probe in which a compound represented by the formula (V) was bound at the same position as that at which DANP was bound in the nucleotide sequence as shown in SEQ ID NO: 7 in Preparation Example 1 of Nucleic Acid Probe was prepared using a DNA synthesizer. Next, PCR reaction was carried out in the same manner as in Test Example 1 of PCR, and the fluorescent intensity was measured. Here, the relative fluorescent intensity in a case where the amount of increase in the fluorescent intensity of DANP after 40 cycles in Test Example 1 of PCR was regarded as 100% was calculated and shown (FIG. 11).

Figure 11:
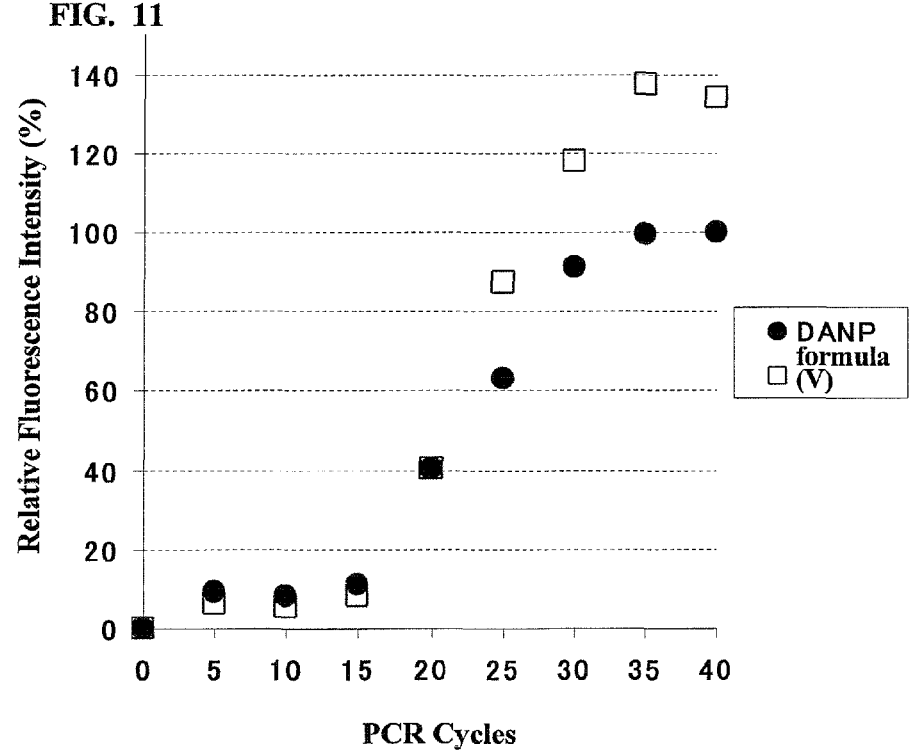
FIG. 11 is a graph showing changes in fluorescent intensities accompanying progress of PCR using the method for detection of the present invention.

According to FIG. 11, increase in the fluorescent intensity was observed with the progress of PCR also in the compound represented by the formula (V), and the degree of increase in the fluorescent intensity was greater than that of DANP (about 130 to about 140%).

INDUSTRIAL APPLICABILITY

According to the detection method of the present invention, a single nucleotide polymorphism in nucleic acids can be highly sensitively detected with simple procedures at low costs. In addition, it is highly probable that not only a single nucleotide polymorphism but also other genes can be detected. Therefore, inexpensive, simple and highly sensitive genetic diagnosis, genetic analysis and the like become possible.

SEQUENCE LISTING FREE TEXT

SEQ ID NO: 1 in the Sequence Listing is a nucleotide sequence of a synthetic DNA (a tag structure of a nucleic acid probe).

SEQ ID NO: 2 in the Sequence Listing is a nucleotide sequence of a synthetic DNA (a template sequence).

SEQ ID NO: 3 in the Sequence Listing is a nucleotide sequence of a synthetic DNA (a cytosine bulge).

SEQ ID NO: 4 in the Sequence Listing is a nucleotide sequence of a synthetic DNA (a thymine bulge).

SEQ ID NO: 5 in the Sequence Listing is a nucleotide sequence of a synthetic DNA (a guanine bulge).

SEQ ID NO: 6 in the Sequence Listing is a nucleotide sequence of a synthetic DNA (an adenine bulge).

SEQ ID NO: 7 in the Sequence Listing is a nucleotide sequence of a synthetic DNA (primer 1).

SEQ ID NO: 8 in the Sequence Listing is a nucleotide sequence of a synthetic DNA (M13M3).

The invention claimed is:

1. A method for detecting a single nucleotide polymorphism in nucleic acids, characterized in that the method comprises:
mixing (A):
i) a nucleic acid probe comprising a nucleotide sequence complementarily hybridizable to an evaluation subject nucleic acid comprising at least one single nucleotide polymorphism, and tagged with a nucleotide sequence of a hairpin structure having a cytosine bulge or thymine bulge at a 5'-terminal thereof,
wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge; or
ii) a nucleic acid probe comprising a nucleotide sequence complementarily hybridizable to an antisense strand of an evaluation subject nucleic acid comprising at least one single nucleotide polymorphism, and tagged with a nucleotide sequence of a hairpin structure having a cytosine bulge or thymine bulge at a 5'-terminal thereof,
wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge; and
(B) the evaluation subject nucleic acids; and
detecting a signal ascribed to the 2,7-diaminonaphthyridine derivative compound due to the disappearance of the above cytosine bulge or thymine bulge when said nucleic acid probe and said evaluation subject nucleic acids are hybridized, thereby evaluating said single nucleotide polymorphism.

2. The method according to claim 1, wherein the method comprises hybridizing at least one of the following 1) to 4):
1) a wild-type evaluation subject nucleic acid comprising a wild-type nucleotide in a single nucleotide polymorphism-existing position, and a nucleic acid probe complementarily hybridizable to the wild-type evaluation subject nucleic acid;
2) a mutant evaluation subject nucleic acid comprising a mutant nucleotide in a single nucleotide polymorphism-existing position, and a nucleic acid probe complementarily hybridizable to the mutant evaluation subject nucleic acid;
3) the wild-type evaluation subject nucleic acid and the nucleic acid probe complementarily hybridizable to the mutant evaluation subject nucleic acid; and
4) the mutant evaluation subject nucleic acid and the nucleic acid probe complementarily hybridizable to the wild-type evaluation subject nucleic acid, and identifying a single nucleotide polymorphism in the evaluation subject nucleic acid, on the basis of a signal ascribed to the 2,7-diaminonaphthyridine derivative compound at the time of hybridization.

3. The method according to claim 1, wherein the signal is fluorescence.

4. The method according to claim 1, wherein the 2,7-diaminonaphthyridine derivative compound is one or more 2,7-diamino-1,8-naphthyridines selected from the group consisting of a compound represented by the following formula (II):

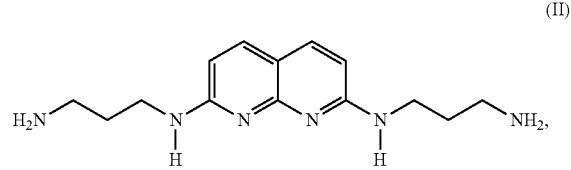 [SMILES: NCCCNc1ccc2ccc(NCCCN)nc2n1]

and
a compound represented by the following formula (V):

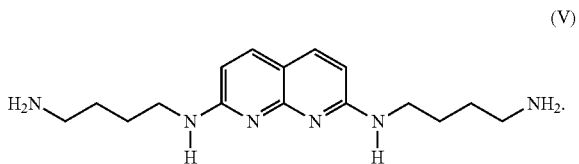 [SMILES: NCCCCNc1ccc2ccc(NCCCCN)nc2n1]

5. A kit for use in a method for detecting a single nucleotide polymorphism in nucleic acids as defined in claim 1, comprising:
i') a nucleic acid probe comprising a nucleotide sequence complementarily hybridizable to an evaluation subject nucleic acid comprising at least one single nucleotide polymorphism, and comprising a wild-type nucleotide in the single nucleotide polymorphism-existing position, and tagged with a nucleotide sequence of a hairpin structure having a cytosine bulge or thymine bulge at a 5'-terminal thereof,
wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge; and
ii') a nucleic acid probe comprising a nucleotide sequence complementarily hybridizable to an antisense strand of an evaluation subject nucleic acid comprising at least one single nucleotide polymorphism, and comprising a wild-type nucleotide in the single nucleotide polymorphism-existing position, and tagged with a nucleotide sequence of a hairpin structure having a cytosine bulge or thymine bulge at a 5'-terminal thereof, wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge; and i'') a nucleic acid probe comprising a nucleotide sequence complementarily hybridizable to an evaluation subject nucleic acid comprising at least one single nucleotide polymorphism, and comprising a mutant nucleotide in the single nucleotide polymorphism-existing position, and tagged with a nucleotide sequence of a hairpin structure having a cytosine bulge or thymine bulge at a 5'-terminal thereof, wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge; and ii'') a nucleic acid probe comprising a nucleotide sequence complementarily hybridizable to an antisense strand of an evaluation subject nucleic acid comprising at least one single nucleotide polymorphism, and comprising a mutant nucleotide in the single nucleotide polymorphism-existing position, and tagged with a nucleotide sequence of a hairpin structure having a cytosine bulge or thymine bulge at a 5'-terminal thereof, wherein a guanine residue is introduced at a position immediately adjoining 5' or 3'-terminal side of the cytosine bulge or thymine bulge, and wherein a 2,7-diaminonaphthyridine derivative compound is immobilized to the cytosine bulge or thymine bulge.

6. A method for detecting a single nucleotide polymorphism in nucleic acids, characterized in that the method comprises:

mixing (A):

i) a nucleic acid probe comprising a nucleotide sequence complementarily hybridizable to an evaluation subject nucleic acid comprising at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; or ii) a nucleic acid probe comprising a nucleotide sequence complementarily hybridizable to an antisense strand of an evaluation subject nucleic acid comprising at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and (B) the evaluation subject nucleic acids; and detecting a signal ascribed to the 2,7-diaminonaphthyridine derivative compound due to the disappearance of the above cytosine bulge or thymine bulge when said nucleic acid probe and said evaluation subject nucleic acids are hybridized, thereby evaluating said single nucleotide polymorphism, and wherein the 2,7-diaminonaphthyridine derivative compound is a compound represented by the following formula (V):

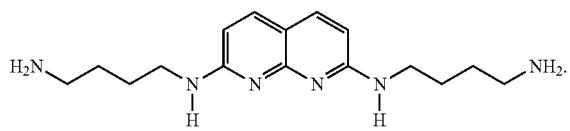

(V)

7. A method for detecting a single nucleotide polymorphism in nucleic acids, characterized in that the method consisting of:

mixing (A):

i) a nucleic acid probe comprising a nucleotide sequence complementarily hybridizable to an evaluation subject nucleic acid comprising at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; or ii) a nucleic acid probe comprising a nucleotide sequence complementarily hybridizable to an antisense strand of an evaluation subject nucleic acid comprising at least one single nucleotide polymorphism, and tagged with a nucleotide sequence of a hairpin structure having a cytosine bulge or thymine bulge at a 5'-terminal thereof, wherein a guanine residue is introduced at a position adjoining 5' or 3'-terminal side of the cytosine bulge or thymine bulge, and wherein a 2,7-diaminonaphthyridine derivative compound is immobilized to the cytosine bulge or thymine bulge; and (B) the evaluation subject nucleic acids; and detecting a single nucleotide polymorphism by measuring a signal ascribed to the 2,7-diaminonaphthyridine derivative compound due to the disappearance of the above cytosine bulge or thymine bulge when said nucleic acid probe and said evaluation subject nucleic acids are hybridized, thereby evaluating said single nucleotide polymorphism, wherein the 2,7-diaminonaphthyridine derivative compound is a compound represented by the following formula (V):

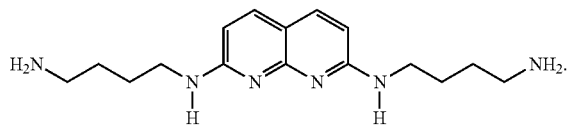

(V)

* * * * *